US009222116B2

(12) United States Patent
Marie et al.

(10) Patent No.: US 9,222,116 B2
(45) Date of Patent: Dec. 29, 2015

(54) MICROFLUIDIC DEVICE AND METHOD FOR PROCESSING OF MACROMOLECULES

(75) Inventors: Rodolphe Marie, Copenhagen V (DK); Anders Kristensen, Copenhagen O (DK); Kristian Hagsted Rasmussen, Soborg (DK); Kalim Ullah Mir, Oxford (GB)

(73) Assignees: DANMARKS TEKNISKE UNIVERSITAT—DTU, Kongens Lyngby (DK); THE CHANCELLOR, MASTERS AND SCHOLARS OF THE UNIVERSITY OF OXFORD, Oxford (GB)

( * ) Notice: Subject to any disclaimer, the term of this patent is extended or adjusted under 35 U.S.C. 154(b) by 144 days.

(21) Appl. No.: 13/881,102

(22) PCT Filed: Oct. 24, 2011

(86) PCT No.: PCT/DK2011/050402
§ 371 (c)(1),
(2), (4) Date: Apr. 23, 2013

(87) PCT Pub. No.: WO2012/055415
PCT Pub. Date: May 3, 2012

(65) Prior Publication Data
US 2013/0224736 A1 Aug. 29, 2013

Related U.S. Application Data

(60) Provisional application No. 61/442,457, filed on Feb. 14, 2011.

(30) Foreign Application Priority Data

Oct. 25, 2010 (GB) .................................... 1017905.9
Feb. 14, 2011 (EP) .................................... 11154384

(51) Int. Cl.
*C12M 1/00* (2006.01)
*C12M 1/34* (2006.01)
(Continued)

(52) U.S. Cl.
CPC ........... *C12P 19/34* (2013.01); *B01L 3/502746* (2013.01); *B01L 3/502761* (2013.01); *C12Q1/6806* (2013.01); *G01N 33/48721* (2013.01); *B01L 2200/06* (2013.01); *B01L 2300/0877* (2013.01); *B01L 2400/086* (2013.01)

(58) Field of Classification Search
USPC .............. 435/6.1, 283.1, 287.2, 288.2, 288.5; 422/68.1, 417; 436/174, 519
See application file for complete search history.

(56) References Cited

U.S. PATENT DOCUMENTS 5,637,458 A * 6/1997 Frankel et al. ............... 435/6.12
2006/0035386 A1 2/2006 Hattori et al.
(Continued)

FOREIGN PATENT DOCUMENTS

WO 2006/052223 A1 5/2006

OTHER PUBLICATIONS

Rasmussen et al, A device for extraction, manipulation and stretching of DNA from single human chromosomes, 2011, Lab Chip, 11, 1431-1433.*

Primary Examiner — Narayan Bhat
(74) Attorney, Agent, or Firm — Nath, Goldberg & Meyer; Jerald L. Meyer; Christopher Thomas

(57) ABSTRACT

A microfluidic device and method for enzymatic processing of ultra-long macromolecules is accomplished using a microfluidic device a reaction chamber with a first manifold, a second manifold, and a plurality of reaction channels. Each reaction channel extends from the first manifold to the second manifold. First inlet and outlet channels fill the reaction channels via the manifolds with one or more macromolecule containers suspended in a first carrier fluid. The first inlet and outlet channels are configured such that a flow is guided through the reaction channels, and an enzymatic reagent is fed to the reaction chamber essentially without displacing the macromolecule containers trapped in the reaction channels. The second set of inlets and outlets are configured such that a flow established from the second inlet to the second outlet is guided through at least one of the manifolds and bypasses the reaction channels.

16 Claims, 6 Drawing Sheets

(51) Int. Cl.
*C12M 3/00* (2006.01)
*G01N 21/75* (2006.01)
*G01N 15/06* (2006.01)
*G01N 1/00* (2006.01)
*G01N 33/554* (2006.01)
*C12P 19/34* (2006.01)
*B01L 3/00* (2006.01)
*C12Q 1/68* (2006.01)
*G01N 33/487* (2006.01)

(56) References Cited

U.S. PATENT DOCUMENTS

| | | |
|---|---|---|
| 2006/0141607 A1 | 6/2006 | Wikswo et al. |
| 2006/0275185 A1 | 12/2006 | Tonkovich et al. |
| 2008/0003689 A1* | 1/2008 | Lee et al. ............ 436/174 |
| 2008/0135101 A1* | 6/2008 | Lee et al. ............ 137/38 |

* cited by examiner

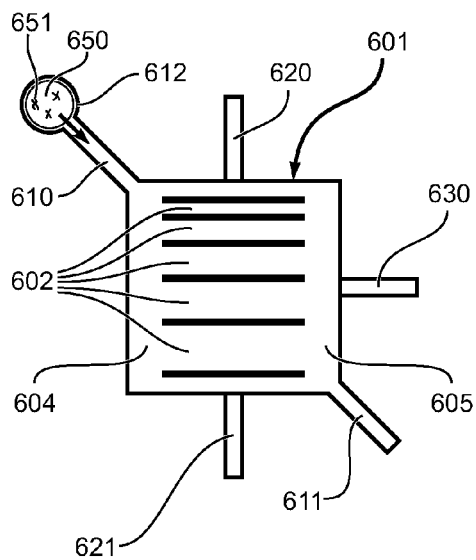
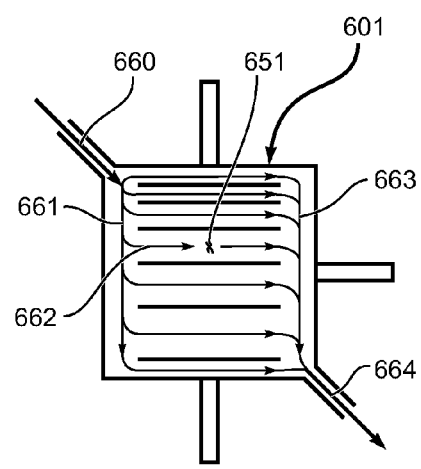
Fig. 6a                Fig. 6b
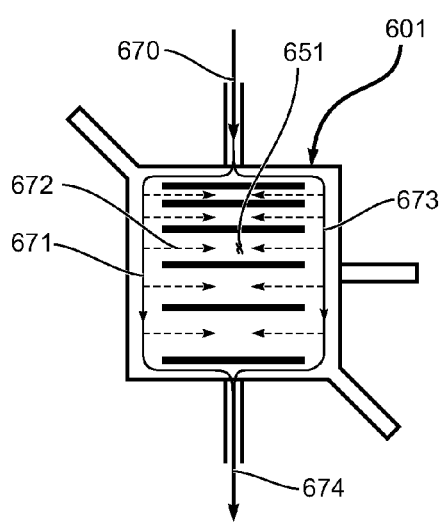
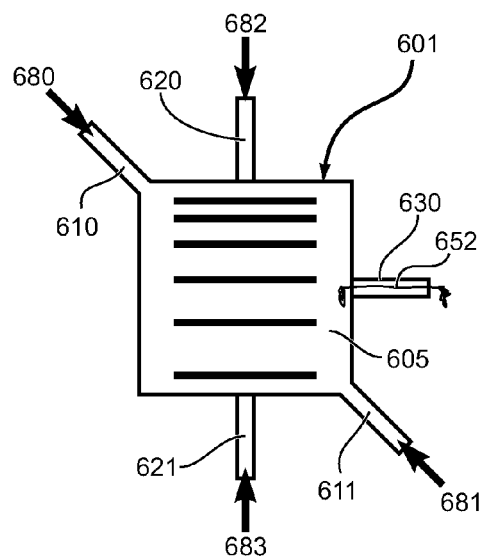
Fig. 6c                Fig. 6d

MICROFLUIDIC DEVICE AND METHOD FOR PROCESSING OF MACROMOLECULES

This is a National Phase Application filed under 35 U.S.C. 371 as a national stage of PCT/DK2011/050402, filed Oct. 24, 2011, and claims priority from United Kingdom Application No. 1017905.9, filed Oct. 25, 2010, U.S. Application No. 61/442,457, filed Feb. 14, 2011 and European Application No.: 11154384.9 filed Feb. 14, 2011, the content of each of which is hereby incorporated by reference in its entirety.

TECHNICAL FIELD

The invention relates to a microfluidic device for enzymatic processing of macromolecules, more particularly for preparation of isolated single macromolecules for subsequent processing. In a further aspect, a method is provided for preparing isolated single macromolecules for subsequent processing. The invention is suited for preparing and processing ultra-long macromolecules, i.e. macromolecules with a length of about 1 million base pairs and more. An example for such macromolecules is DNA.

According to a further aspect, the present invention relates to systems, apparatus, kits, algorithms and methods for handling, preparing analysing and characterizing (in any order) biological samples. The invention also describes uses of the invention, particularly in relation to nucleic acid sequencing technologies.

BACKGROUND

In the recent decades, micro- and nanofluidic devices and methods have been developed for integrating, miniaturising and automating numerous laboratory tasks. Furthermore, due to the characteristic length scales involved, analysis tasks not previously available have been made possible.

Considerable efforts have been directed to providing a reliable, rapid and affordable analysis of very long macromolecules, such as single DNA molecules, including amplification and/or sequencing steps. However, the maximum fragment lengths analysed by existing methods, are typically limited to about 35-1000 base pairs as compared to the length of bacterial DNA of about 1-10 million base pairs, and at least 50 million base pairs of a complete human DNA molecule.

A recent article on "Single molecule linear analysis of DNA in nano-channel labelled with sequence specific fluorescent probes", published in 2010 in Nucleic Acids Research by S. K. Das et al., discloses a nanofluidic method of analysing DNA molecules. The DNA molecules analysed have all a length less than 200 kilo base pairs. A further article on nanofluidic analysis of DNA by Reisner and co-workers, published in Proceedings of the National Academy of Sciences of the USA, vol. 107, p. 13294, 2010, discloses a method for analysing DNA applicable to long DNA molecules, where "long" refers to a length of about 100 kilo base pairs.

It is one of the merits of the present invention to recognise, that the main factor limiting the length of the fragments analysed in a nanofluidic system lies in the sample preparation and transfer steps. As a principal reason for this limitation, the fragility of isolated DNA molecules or similar long macromolecules, due to shearing forces acting on the DNA, has been identified. According to the present invention, the sample preparation and transfer steps are thus identified to be critical for increasing the fragment length that can be analysed in micro- and nanofluidic systems, and eventually being able to process, e.g. for sequencing or amplification, a complete isolated DNA molecule or similar long macromolecule.

A chromosome prior to replication comprises a single length of DNA. The ability to visualize the DNA from each chromosome, from one end to the other, would enable the native long-range organization of the genome and its variation between homologous chromosomes and between individuals to be investigated. Entropic confinement in nanochannels/grooves, as demonstrated for bacteriophage genomes (<200 Kbp length), forces DNA into an extended conformation co-linear with the information encoded therein. However, to linearize whole large genomes (e.g. Human), direct from source without cloning, two problems must be considered: Firstly, during extraction or loading into a device, genomic DNA can become fragmented due to shear forces, and secondly, DNA tends to form folded, globular states in solution rather than the extended conformation. Although methods for mapping sequence motifs and patterns (Neely et al Chem. Sci. 2010; Xiao et al Nucleic Acids Res. 35: e16 2007; Reisner et al PNAS107(30):13294-9) on linearized DNA have been developed, new approaches are needed to handle, if not whole chromosomal lengths of human DNA, then portions of chromosomes that are large enough to span the haplotype blocks and much of the structural variation found in large diploid genomes.

Moreover genome analysis methods with minimal sample preparation are needed. Direct single molecule analysis of genomic DNA can achieve this; recently a whole genome has been sequenced using single molecule technology (Pushkarov et al, Nature Biotechnology 27: 847). Even so, in current methods, DNA extraction is done off-chip and the DNA handling (e.g. pipetting) leads to reduction in size of the genome fragments due to fragmentation by shearing.

There is a pronounced need for single molecule analysis of long macromolecules. For example, there are an estimated 200 cell types in the human body. However, all cells within a seemingly homogeneous population of a given a cell type are not necessarily alike. Stochastic expression at the gene and protein level is well documented. Stochastic effects lead to widely differing responses to stimuli: fast, slow, extreme or subdued. Ensemble analysis of cell populations masks the variation that is clearly evident when individual cells from a population are analysed.

There is substantial heterogeneity between cells in a tumour biopsy, including differences in chromosome number (aneuploidy), mutational profiles, methylation profiles and expression at the RNA and protein level. Analysis of single cells within tumours is important for understanding tumour pathology and is expected to contribute to cancer diagnosis, staging, and prognosis. Biopsies may contain on the order of 10,000 cells. Systematic, high throughput and preferably automatable analysis is therefore needed to address the population cell by cell.

In addition single cell analysis is important for genetic diagnosis, particularly for pre-implantation genetic analysis, which in the future may require analysis of more than one or a few genes, as the scientific community makes increasingly more connections between genotype and phenotype.

In many cases sample material is limiting, for example from archived material or for the analysis of fetal material in a mothers circulating blood or shed tumour cells or metastatic cells in circulating blood. In these cases better methods are needed for analysis of single or a few cells or a small amount of material. In the case of analysis of material in circulating blood the task may be compared to finding a needle in a haystack because the target material is a small fraction of a complex sample.

The genome and its epigenetic modifications can be analysed by modern genomic methods, the most comprehensive approach being complete genome sequencing. However, despite the emergence of technologies that have increased throughput and spectacularly lowered sequencing cost, a number of bottlenecks remain that serve as barriers to the effective translation of genomic knowledge. Although much attention has been given to throughput/cost of the sequencing process itself, the same cannot be said of preparation of the sample for sequencing. A first bottleneck is that sequencing technologies require days of upfront sample preparation. A second bottleneck is that upfront sample processing is further increased when goal is to sequence selected parts of the genome. A third bottleneck arises because all the existing technologies produce short sequence reads and thus genome assembly relies on comparing reads to the reference genome. But since the reference sequence is a composite of several genomes, such comparisons do not reveal the phenotypically significant structural variation that exists between individual genomes (rearrangements, copy number, translocations, inversions).

As mentioned above, it is one of the merits of the present invention to recognise, that the main factor limiting the length of the fragments analysed in a micro- and/or nanofluidic system lies in the sample preparation and transfer steps.

With this insight in mind, the object of the present invention is providing an improved technique for preparing long macromolecules for subsequent processing in a micro- and/or nanofluidic device overcoming the problems of the prior art or at least providing an alternative.

DISCLOSURE OF THE INVENTION

According to a first aspect of the invention, a microfluidic device for enzymatic processing of macromolecules comprises a reaction chamber with a first manifold, a second manifold, and a plurality of reaction channels, each reaction channel extending from the first manifold to the second manifold. The device further comprises first inlet and outlet channels for filling the reaction channels via the manifolds with one or more macromolecule containers suspended in a first carrier fluid, wherein the first inlet and outlet channels are configured such that a flow established from the first set of inlets to the first set of outlets is guided through the reaction channels. The device further comprises second inlet and outlet channels for feeding an enzymatic reagent to the reaction chamber essentially without displacing the macromolecule containers trapped in the reaction channels, wherein the second set of inlets and outlets are configured such that a flow established from the second inlet to the second outlet is guided through at least one of the manifolds and bypasses the reaction channels.

The microfluidic device is filled through an input port with a sample solution containing macromolecule containers. The input port is via the one or more first inlet channels connected to the first manifold, which via the reaction channels ("isolation zones") in the reaction chamber ("trap area") is in fluid communication with the second manifold, which in turn via the first outlet channel is connected to an outlet port. The reaction channels are filled with the sample solution and a flow of sample solution is established from the inlet port to the outlet port. The flow of sample solution thus carries at least one macromolecule container into at least one of the reaction channels. When an isolated macromolecule is identified to be present in one of the reaction channels, the flow of sample solution is stopped and a flow of enzymatic reagent is established from the one or more second inlet channels via the manifolds to the one or more second outlet channels.

The second inlet and outlet channels are configured for feeding the enzymatic reagent to the reaction chamber without displacing the macromolecules trapped in the reaction channels. Displacement of the trapped macromolecules is avoided by carefully balancing the pressure in the first and second manifolds, i.e. the pressure applied on either end of each of the reaction channels. The reaction channels thus form a stagnant volume of the flow and only the sample solution in the manifolds is replaced by the enzymatic reagent. The enzymatic reagent diffuses from the manifolds into the reaction channels, and thus also into the reaction channel comprising the identified isolated macromolecule container. The enzymatic reagent interacts with the isolated macromolecule container, thereby producing an intact isolated macromolecule in the reaction channel. The isolated macromolecule may then by fluid handling be retrieved from the reaction channel and extracted from the reaction chamber in order to transfer the macromolecule to its destination for single molecule analysis or any other single molecule processing in one or more subsequent stages. The second inlet and outlet channels may also be used for flushing buffer solutions and/or feeding any reagents, to be applied to the macromolecule container and/or to the released macromolecule.

Preferably, the second inlet and/or outlet channels are made shallower than the microchannels in the reaction chamber. Thereby, flow of sample fluid into the reagent channels is avoided or at least kept at a minimum.

An important advantage of the device according to the invention is that sample macromolecules are provided to the input of the device in a macromolecule container. The macromolecule container protects the macromolecule from mechanical shearing during sample preparation and handling of the macromolecules, e.g. by pipetting. The macromolecule container thus acts as a "carrier" for the macromolecule. A macromolecule container may be formed by encapsulation of the macromolecule, by complexing the macromolecule with a protein scaffold or by complexing the macromolecule with polycations. A DNA molecule may, for example be encapsulated by a cell wall, in a nucleus, or carried by cell extract, preferably a metaphase chromosome. Preferably, DNA molecules are provided to the microfluidic device in a solution containing chromosomes acting as a container for the DNA molecules. In the case where cells are loaded into the device, metaphase chromosomes are obtained from the cell on-chip before releasing DNA from the chromosomes. Where cell extract is loaded, DNA can be released directly from the chromosomes. Alternatively a macromolecule container may be formed by complexing the macromolecule with a protein scaffold or in some cases with polycations, such as spermine or spermidine.

The macromolecules are released from their container on-chip where shearing forces are minimal and/or are controlled. Releasing DNA from metaphase chromosome comprises the addition of one or more enzymatic reagents. This may include the addition of proteases. The preferred protease is Proteinase K. Other protease may also be useful (e.g. Trypsin). It may also include the addition of topoisomerases before or after adding the protease. Where topoisomerase is added after protease care is taken to kill the activity of the protease and/or to remove the protease. Preferably, the proteases used are appropriate for digesting at least histones or protamine. Releasing DNA may comprise the creation of a substantially naked DNA molecule, essentially devoid of proteins. However, in some cases it may be desirable to retain binding of one or more class of proteins to the DNA. Therefore, releasing DNA may alternatively comprise the creation of chromatin fibres to which proteins are still associated.

Once released, the isolated macromolecule may be manipulated by means of on-chip fluid handling and transferred to subsequent processing/analysis stages. Thereby the mechanical forces exerted on the released macromolecule may be controlled to a level so as to avoid unintended breaking of the macromolecule. The device according to the invention may thus prepare isolated macromolecules with a length that by far exceeds the length of macromolecules prepared by known techniques.

The invention thus provides a device, system and method for releasing macromolecules, such as biomolecules, on chip from small amounts of sample material, single cells, nuclei or chromosomes in a manner that keeps the macromolecules substantially intact. In particular, in an embodiment applied to genomic DNA, megabase lengths of DNA can be kept intact. Advantageously for this embodiment, following releasing of the DNA, the DNA is linearly elongated and displayed for detection. In a further embodiment the chip design allows reagents to be flushed over the DNA and allows features of interest to be labelled and then mapped. Events along the span of the DNA region being imaged can be followed in real-time. The invention provides an unprecedentedly long-range view of the genome, which encompasses the haplotype blocks as well as the structural organization of the genome. The long-range view will facilitate the de novo identification of a significant amount of previously characterized and uncharacterised copy number/structural variation. Furthermore, the mapping can be used to barcode individual genome fragments, which enables parts of the genome, bearing specific map patterns to be selected. After analysis, individual megabase length molecules can be transported to an output port of the chip, from where they can be further processed. For example, the DNA can be isothermally amplified in- or off-chip. The amplified DNA can then be collected from the output port and subjected to further molecular analysis including sequencing by any available method. Also a DNA fragment sent to the outlet port can be a component in the assembly of artificial chromosomes or used for synthesis of complex macromolecules.

Advantageously, the method of the invention may be used at the front-end of sequencing pipelines and significantly enhances the quality and throughput of DNA sequencing. In one embodiment of the invention a micro-/nano-fluidic device processes a population of individual cells in a high-throughput manner: releasing and purifying DNA from each cell and preparing the DNA through to the final steps for sequencing. Moreover, the sample preparation is done in a highly innovative way which has the double side-benefit that the long-range haplotype map of the genome can be obtained and specific parts of the genome can be selected for sequencing. It is the downstream choice of the investigator whether to collect data separately from single cells or whether to amalgamate the data from the population of cells. If the latter, the investigator still benefits because less sample material is required.

As well as applications in the research environment the microfluidic or micro/nanofluidic devices of this invention can be used as part of point-of-care systems for medical testing as well as devices for monitoring samples in the field or in various industries (e.g. water-treatment, food processing).

In a preferred embodiment of a device according to the invention, a single pair of second inlet and outlet channels is provided and the reaction chamber is essentially symmetric with respect to a mirror axis connecting said second inlet and second outlet, a longitudinal axis of the reaction channels being oriented essentially transverse to the mirror axis.

The single pair of second inlet and outlet channels has a single second inlet and a single second outlet. The second inlet channel is via an inlet branch symmetrically connected to both the first and the second manifolds. The second outlet channel is via an outlet branch symmetrically connected to both the first and the second manifolds.

The second inlet and the second outlet are thus configured to supply enzymatic reagent symmetrically to the manifolds on either end of the reaction channels, thereby maintaining substantially equal pressure, equal flow rate, and thereby for each reaction channel a balanced reagent concentration on either end.

Alternatively, an embodiment of a device according to the invention may comprise a mirror-symmetric trap area, wherein the reaction channels extend essentially transverse to the mirror axis from a first manifold to a second manifold, and wherein each of the manifolds is provided with an inlet at a first end of the manifold and an outlet at a second end opposite to the first end. In this embodiment, the reaction channels of the trap area may be loaded with a sample fluid containing macromolecule containers by establishing a diagonal flow through the reaction chamber, i.e. from an inlet of one of the manifolds (first/second manifold) via the reaction channels to an outlet of a different manifold (second/first manifold). Once the presence of at least one target macromolecule container has been determined, i.e. the trapping of a macromolecule container in a reaction channel, the filling flow is stopped and a secondary flow of flushing agents/buffers and/or reagents may be established. Any flushing agents/buffers and/or reagents are provided by a symmetric flow bypassing the reaction channels, i.e. where a flow is driven through each of the manifolds from the respective inlet to the respective outlet without passing through a reaction channel. The pressure in the manifolds is balanced with respect to each other, such that at the same pressure is present at either end of a given reaction channel, thereby avoiding any flow/displacement of the trapped target macromolecule in the reaction channel. The reagent required for releasing the macromolecule from its container is supplied via diffusion from the manifold into the reaction channel.

In a further embodiment of a device according to the invention, the device is provided with a viewport in the region of the reaction channels, the view port allowing for the visual detection of a trapped macromolecule container in at least one of the reaction channels. The visual detection is typically performed by monitoring one or more of the reaction channels during filling of the channels.

The term "visual" comprises any form of optical observation, and in particular any microscopic imaging technique and may, advantageously be combined with a machine vision system comprising recognition modules providing target detection signals representing the presence of a target macromolecule/macromolecule container. A machine vision system may also provide further signals responsive to the visual monitoring of any process steps performed on the target following detection, including releasing the macromolecule from its container, labelling, fragmenting, de-/re-naturation and/or transferring of the released macromolecule. Alternatively, target detection signals and any further monitoring signals may be provided by other means, such as integrated or external electrical and/or magnetic sensors. Any detection and/or further monitoring signals may be used as input to a control unit for controlling the processing in an auto-mated manner.

In a further embodiment of a device according to the invention, the total effective cross-sectional area for flow through the reaction chamber in the region of the reaction channels is enlarged as compared to the first inlet channel by a ratio of at least 2:1, alternatively at least 5:1, or alternatively at least 10:1. For a given throughput this reduces the flow velocity of the sample fluid, thereby facilitating the detection of a target macromolecule.

In a further embodiment of a device according to the invention, the flow resistance of reaction channels is decreased with increasing distance from the first inlet channel. When establishing a filling flow passing through the reaction channels, a pressure drop occurs along the manifolds, wherein the pressure decreases for increasing distance from the inlet channel. Consequently different driving conditions for the flow through the reaction channels may occur. To counter this effect, and to equalize the flow through the reaction channels with respect to each other, the resistance of the reaction channels is decreased, advantageously by increasing the width of the reaction channels with increasing distance from the first inlet channel. Advantageously, the distance is increased according to a linear relationship. Equalizing the filling flow has the advantage that it facilitates detection of target macromolecule containers in any of the reaction channels.

In a further embodiment of a device according to the invention, the device only comprises passive microfluidic components. An important advantage of the device according to the invention is that it does not require any active fluidic components on chip for trapping the macromolecule container, and for releasing and retrieving the isolated macromolecule. Any flow driving and control components, such as pumps, valves or the like can thus be provided external to the device. The device only comprising passive microfluidic components can thus be provided e.g. as a chip interacting/interfacing with an analysis apparatus providing such infrastructure, whereas the chip is produced cheaply, e.g. as a disposable consumable.

In a further embodiment of a device according to the invention, the reaction chamber has a rectangular layout, the rectangle having a first edge, a second edge parallel thereto, and a third and a fourth edge essentially perpendicular to the first and second edges, the first and second manifold extending along the first and second edge, respectively, the reaction channels extending from the first to the second manifold in a direction essentially parallel to the third and fourth edge, the first inlet and outlet being arranged at diagonally opposing corners of the rectangle, and the second inlet and outlet being arranged at the third and fourth edge respectively, wherein both the second inlet and the second outlet are in symmetric fluid communication with both the first and the second manifold through edge channels extending parallel to the reaction channels along the third and fourth edge.

This configuration allows in a simple manner for establishing a diagonal filling flow, i.e. a flow passing from a first inlet via a first manifold, through essentially all reaction channels, and via a second manifold to an outlet channel.

According to a broader aspect of this embodiment, the first inlet and outlet channels are arranged at opposing edges of the rectangular reaction chamber. Preferably, at least a first inlet channel is provided at the first edge and at least a first outlet channel is provided at the second edge opposite to the first edge. Advantageously, the axis connecting the first inlet and outlet channels is not a symmetry axis of the reaction chamber. The asymmetric arrangement has the advantage of promoting distribution of the injected sample fluid over the reaction channels.

Preferably, the filling flow is injected from the first inlet into the reaction chamber at an angle that is inclined with respect to the direction of the flow barriers defining the reaction channels. Injecting the filling flow at an angle with respect to the flow barriers/reaction channels further promotes distribution of the sample fluid over the reaction channels.

Advantageously said angle of injection is selected from the range between 10 to 90 degrees, alternatively from the range between 30 to 60 degrees, preferably about 45 degrees. For reasons of disambiguation only angles between 0 and 90 degrees are recited. Angles in excess of 90 degrees are mapped back to said range between 0 and 90 degrees by always measuring the smallest angle between the direction of injection and the direction of the flow barriers defining the reaction channel walls.

The single pair of second inlet and outlet channels is in symmetric fluid communication with the first and second manifolds. This means that by injecting a fluid through the second inlet channel, a symmetric pressure distribution is established in the reaction chamber, and a balanced pressure level is established on either end of each of the reaction channels. While the pressure may drop in the manifolds along the direction of flow, the device is configured such that the pressure drop in one of the manifolds is a mirror of the pressure drop in the other manifold with respect to the symmetry axis of the reaction chamber.

Operation of the device is particularly simple and reliable, because it only requires simple actuation of external valves and/or flow driving components, yet keeping sample fluids and reagent fluids well separated. Correct establishing of the appropriate type of flow for sample fluids (diagonal flow) and for reagent fluids (symmetric flow bypassing the reaction channels) is taken care off by the geometric lay-out of the device.

In a further embodiment of a device according to the invention, the device further comprises an extraction channel connected to one of the manifolds.

Reaction products/fractioned components of the macromolecule may be collected and extracted from the reaction chamber through a suitable extraction channel connected to one of the manifolds, and either directly transferred to a subsequent processing stage or retrieved from an extraction port.

Preferably, the extraction channel is a wide, but shallow channel. In order to stretch out the macromolecule in the extraction channel, the height/depth of the extraction channel should be in the same length scale as the persistence length of the macromolecule, e.g. the characteristic length of the macromolecule representing the flexibility of the macromolecule. For double stranded DNA, this length is about 64 nm depending on salt concentration in the carrier fluid. A preferred range for the height/depth of the extraction channel is between 50 nm and 100 nm. The width of the extraction channel should be larger than this characteristic length so that the macromolecule can rearrange in order to resolve folds or similar disarrangements.

In order to facilitate high volume production of the device, defining the lateral dimensions of the device including the extraction channel should be compatible with microscale pattern transfer techniques, i.e. patterning techniques for reliably producing lateral feature widths of about 1 µm and above, such as UV-lithography, microinjection moulding or any other high volume micro-fabrication technique. In order to achieve a satisfactory yield in a laboratory scale production, the extraction channel width is typically larger than 4 µm. Furthermore, an extraction channel nanoslit with a microscale width is advantageous for avoiding excessive pressure build-up in the device and the associated fluidic system under operation. Therefore, the width of the extraction channel is preferably also adapted according to fluidic design considerations for a given type of application. In order to shunt a macromolecule into and through the shallow extraction channel, it is desirable to achieve a reasonable flow rate through the extraction channel, thereby avoiding excessive pressure build-up inside the device. Increasing the width of the channel is a mean to limit the maximum pressure to achieve the desired flow rate as high pressure can jeopardize the sealing of the device or the microfluidic handling system, such as pumps, valves, fluidic connectors, and the like.

As mentioned above, the device according to the invention may be integrated into an automated system for enzymatic processing and analysis of macromolecules. The automated system may comprise automated fluid handling for handling sample and reagent fluids. Any active components of the automated fluid handling system may be arranged external to the microfluidic device and interface with the microfluidic device through any known type of fluid connection technology.

A system for enzymatic processing of macromolecules comprising a device according to the invention may further comprise a machine vision system for the automated detection of a trapped macromolecule container in at least one of the reaction channels. A suitable machine vision system includes appropriate optics for imaging the macromolecule on an electronic image sensor using any known microscopic technique.

Furthermore, a system using the microfluidic device according to the present invention may comprise a nanofluidic processing/analysis portion, such as a sequencing portion or an amplification stage, arranged in direct extension of the extraction channel.

According to a further aspect of the invention, a method for preparing isolated macromolecules is provided. The method has the same advantages has mentioned above with reference to a microfluidic device for enzymatic processing of macromolecules.

A method for preparing isolated macromolecules and using a microfluidic device according to any of the above-mentioned embodiments comprises the steps of
a) at an input port connected to the first inlet, providing a first fluid containing macromolecule containers,
b) establishing a flow of the first fluid from the first inlet, via the first manifold, through the reaction channels, and via the second manifold to the first outlet,
c) stopping the flow, when a macromolecule container is detected in one of the reaction channels, thereby trapping the macromolecule container in said reaction channel,
d) at an input port connected to the second inlet, providing a second fluid containing an enzymatic reagent,
e) in at least one of the manifolds, replacing the first fluid by the second fluid by establishing a flow from the second inlet to the second outlet, wherein the flow of the second fluid essentially by-passes the reaction channels, and
f) allowing the enzymatic reagent to diffuse from the at least one manifold into the reaction channels to perform an enzymatic reaction releasing an isolated macromolecule from its container.

In a further embodiment of a method according to the invention, the macromolecule container is a metaphase chromosome and the macromolecule is a DNA-molecule.

In a further embodiment of a method according to the invention, a pre-defined level of enzyme concentration is maintained in the at least one manifold by maintaining in the at least one manifold a continuous flow of reagent with a pre-defined enzyme concentration.

In a further embodiment of a method according to the invention, in step c), trapping of the macromolecule container in one of the reaction channels is visually detected by an operator and/or by means of a machine vision system.

In a further embodiment of a method according to the invention, in step e) the first fluid is replaced by the second fluid essentially simultaneously in both manifolds, wherein at least for the reaction channel comprising the trapped macromolecule container, the hydrostatic pressures on either end of said reaction channel are balanced during said replacement.

In a further embodiment of a method according to the invention, the method further comprises the step of
g) transferring the isolated macromolecule via an extraction channel to a subsequent processing step, such as sequencing and/or amplification.

BRIEF DESCRIPTION OF THE DRAWINGS

In the following, the invention is described in detail with reference to schematic drawings, where like numerals refer to like parts. The drawings show on
FIG. 1 an embodiment of a microfluidic device according to the invention,
FIG. 2 a detail of the embodiment of the device shown in FIG. 1,
FIG. 3 cross-sectional view of the reaction chamber along line III-III in FIG. 2,
FIG. 4 cross-sectional view of the device along line IV-IV in FIG. 2,
FIG. 5 detail of the reaction chamber region of an alternative embodiment of a microfluidic device according to the invention in (a) a first operational state, and (b) in a second operational state,
FIG. 6a-6d different operational states for a device according to another embodiment of the invention,
FIG. 7 a sequence of micrographs showing the filling of the manifolds with an enzymatic reagent and the diffusion thereof into the reaction channels,
FIG. 8 micrographs showing digestion of chromosomes in the reaction chamber,
FIG. 9 micrographs showing A) a released DNA molecule being shunted to the extraction port, and B) and C) details of the released DNA molecule in the extraction port, and
FIG. 10 a further embodiment of a device according to the invention.

DETAILED DESCRIPTION OF THE INVENTION

Figure 1:
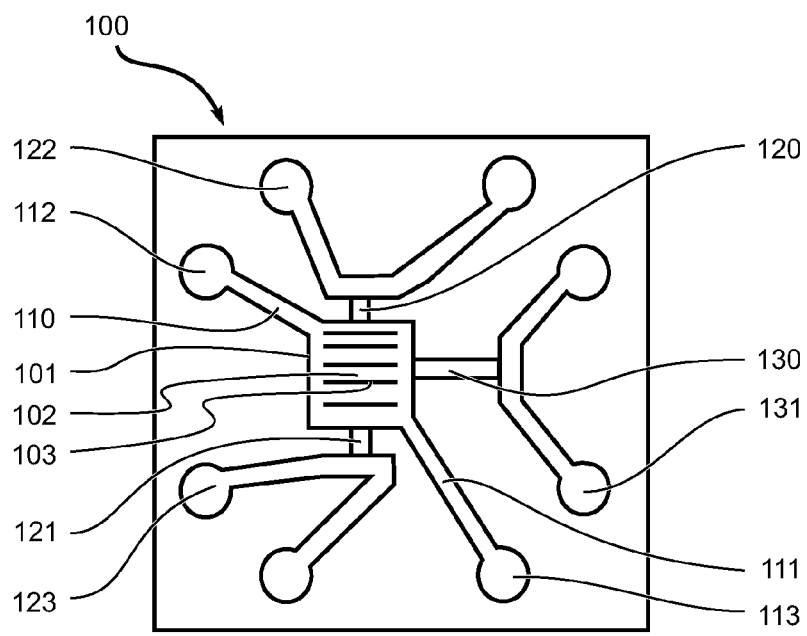

FIG. 1 shows schematically a microfluidic device 100 according to one embodiment of the invention. At the centre, the device 100 comprises a reaction chamber 101 (trap area) comprising reaction channels 102 defined by flow barriers 103. A fluid sample may be loaded at a sample input port 112 and transferred to the reaction chamber 101 via a first inlet channel 110. The sample fluid may leave the reaction chamber 101 via a first outlet channel 111 and is discharged at a sample output port 113. Reagents may be provided in the form of a reagent fluid at a reagent input port 122 and are injected into to the reaction chamber 101 via a second inlet channel 120. A flow of reagent fluid may leave the reaction chamber 101 via a second outlet channel 121 and is discharged through a reagent output port 123. Processed samples may be retrieved through an extraction channel 130 and output at an extraction port 131.

Figure 2:
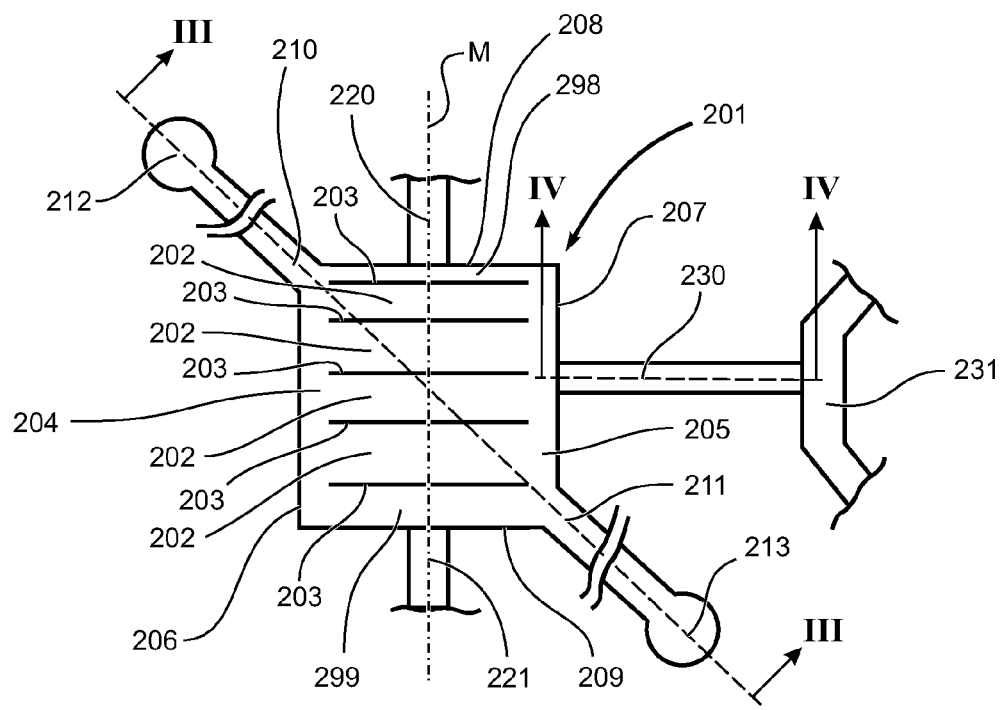

FIG. 2 shows schematically a detail of the reaction chamber portion 201 of a microfluidic device 100 according to one embodiment of the invention. Notably, the reaction chamber 201 has a square lay-out with a first edge 206, a second edge 207 parallel thereto, and a third edge 208 and a fourth edge 209 essentially perpendicular to the first and second edges 206, 207. The reaction chamber 201 comprises a first manifold 204 and a second manifold 205 extending along the first edge 206 and the second edge 207, respectively. The reaction chamber 201 further comprises reaction channels 202 defined by flow barriers 203 and extending from the first manifold 204 to the second manifold 205 in a direction essentially parallel to the third and fourth edge 208, 209. A first inlet 210 and outlet 211 are arranged at diagonally opposing corners of the square, wherein the principal axis of the first inlet channel 210 and the second outlet channel 213 are oriented at an angle of about 45 degrees with respect to the flow barriers 203 and thus with respect to the reaction channels 202. This arrangement of reaction chamber layout and sample fluid inlet/outlet configuration provides for an improved distribution of the sample fluid flow throughout the reaction chamber 201, thereby facilitating an even filling of the reaction channels 202.

A second inlet 220 and outlet 221 are arranged at the third and fourth edge 208, 209, respectively. The reaction chamber is essentially symmetric with respect to a mirror axis M connecting the second inlet 220 and the second outlet 221, and a longitudinal axis of the reaction channels 202 is oriented perpendicular to the mirror axis M. Both the second inlet 220 and the second outlet 221 are in symmetric fluid communication with both the first and the second manifold 204, 205 through edge channels 298, 299 extending parallel to the reaction channels 202 along the third and fourth edge 208, 209.

The reaction channels 202 thus act as zones for isolation of a macromolecule container (e.g. chromosome, nucleus, or cell) from which a macromolecule/polymer (e.g. Nuclear Acid) can be released. The released macromolecule can then be passed to an extraction channel 230 from where it may be retrieved for subsequent processing, for example through an extraction port 231.

Figure 3:
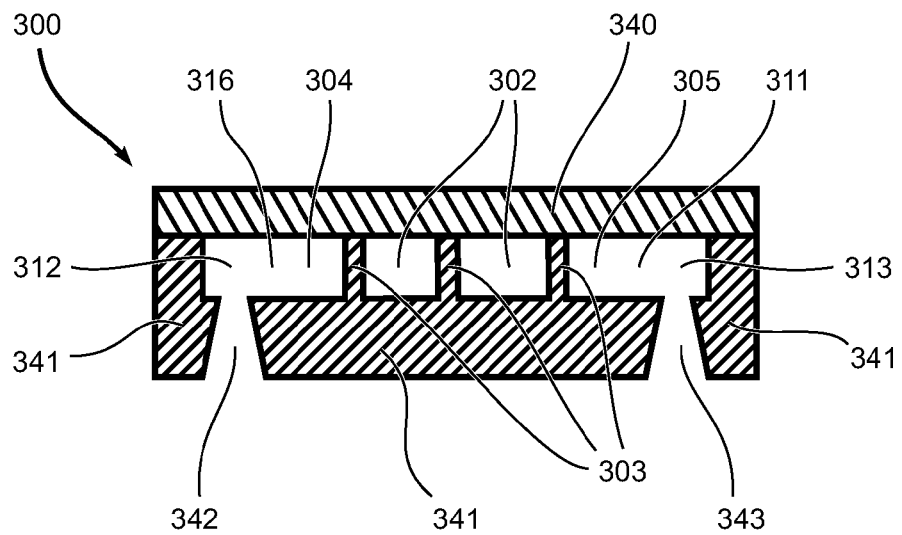

FIG. 3 shows schematically a cross-sectional view of the reaction chamber along line III-III in FIG. 2. The microfluidic device 300 comprises a micro-structured first part 341 with access holes 342, 343 for access to the sample input and output ports 312, 313, respectively. A cover part 340 is bonded to the first part 341 so as to define closed microfluidic channels. The cross-section passes from the sample inlet port 312 through the first inlet channel 310, via the first manifold 304, through reaction channels 302 defined by flow barriers 303, via the second manifold 305, and through the first outlet channel 311 to the sample output port 313.

Figure 4:
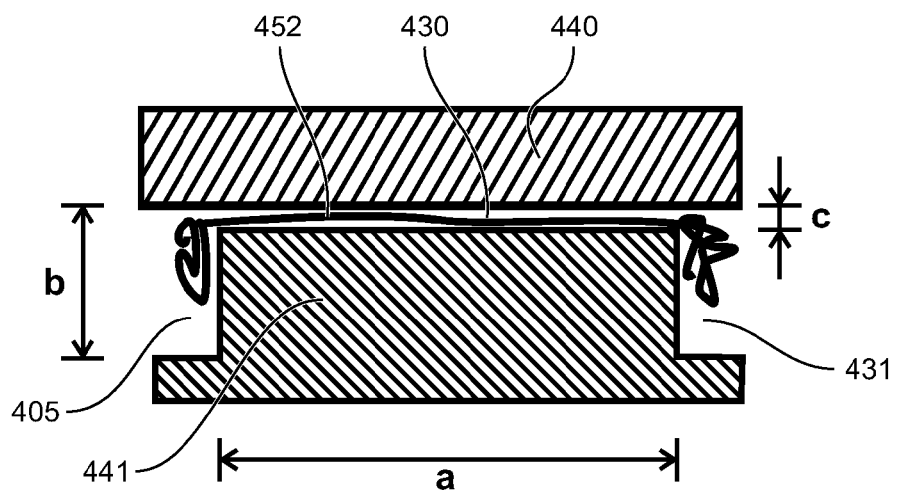

FIG. 4 shows schematically a cross-sectional view of the device along line IV-IV in FIG. 2. As in mentioned above with respect to FIG. 3, a micro-structured first part 441 defines together with a cover part 440 the fluid channels of the device. The cross-section illustrates how a released macromolecule 452 is transferred from a coiled state in the second manifold 405 to a linearized state in the extraction channel 430 and further to a recoiled state in an extraction port 431. Note, that the first part 431 in lateral directions (i.e. in the plane of FIG. 2) may be patterned with micron-scale resolution techniques whereas in a vertical direction (i.e. in the plane of the cross-sections of FIG. 3 or FIG. 4) shallow milling may be performed to achieve nano-scale structures in some regions, and micron-scale milling may be performed to obtain deeper channels in other regions. In particular, the extraction channel 430 may have a depth c of 100 nm, whereas the depth of the manifold 405 is for example 10 µm. Also the length a of the extraction channel is chosen depending on the application, and is for example 450 µm, but may also be several millimeters or even a few centimeters.

FIG. 5 shows schematically a detail of the reaction chamber region of an alternative embodiment of a microfluidic device according to the invention. Like the embodiment of FIG. 2, the reaction chamber 501 has a square layout with a first manifold 504 and a second manifold 505, both manifolds 504, 505 extending in a first direction along parallel edges of the square. Reaction channels 502 are defined by flow barriers 503 extending perpendicular thereto from the first manifold 504 to the second manifold 505. s 502. A shallow extraction channel 530 is centrally connected to the second manifold 505.

The embodiment of FIG. 5 differs from the embodiment of FIG. 2 in the arrangement of fluid connection channels 510, 511, 514, 515 connecting the reaction chamber to fluidic interface ports (not shown) of the device. The four fluid connection channels 510, 511, 514, 515 extend outwardly from the four corners of the rectangle, one connection channel from each corner, at an angle of between 30 and 60 degrees, preferably about 45 degrees with respect to the direction of the reaction channel. As shown in the schematic drawing, the connection channels 510, 511, 514, 515 have essentially the same dimensions and are arranged mirror symmetrically at least with respect to a centre axis M.

Figure 5A:
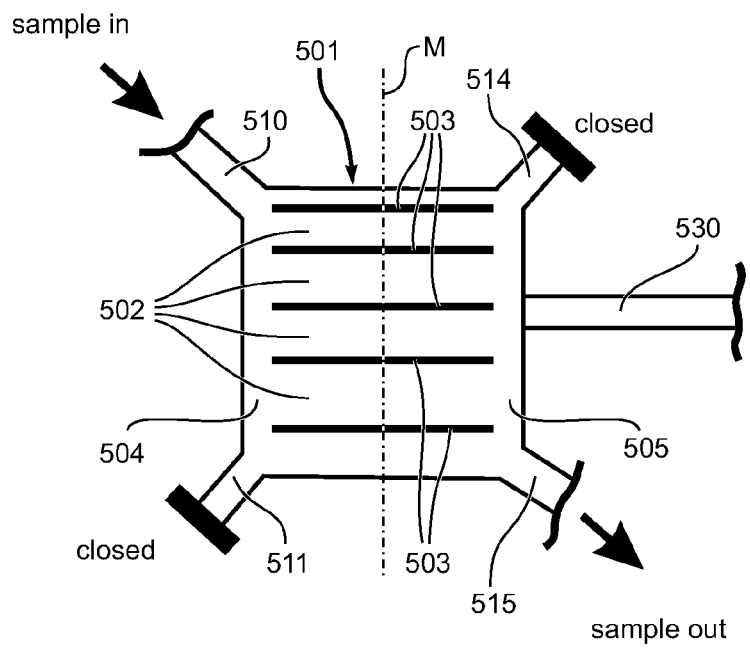

FIG. 5a shows a first operational state, where a diagonal flow is established for filling the reaction chamber 501 with a sample fluid. Due to the symmetry of the device, any of the connection channels 510, 511, 514, 515 may be chosen as a first inlet channel for injecting the sample fluid (here 510). A diagonal flow is established by using the connection channel at the diagonally opposing corner as the first outlet channel (here 515), while keeping the two other connection channels blocked/closed (here 511, 514).

Figure 5B:
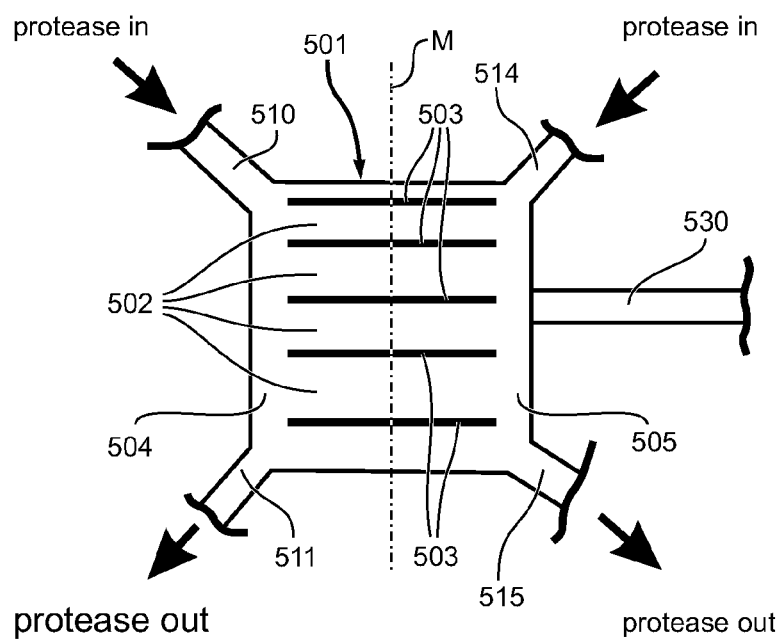

FIG. 5b shows a second operational state, where parallel reagent flows are established in both manifolds 504, 505 by simultaneously injecting reagent into the first manifold 504 and the second manifold 505 through connection channels at the same edge and discharging the reagent through corresponding connection channel at the opposite edge. In the operational state shown in FIG. 5b, reagent is injected from connection channel 510 acting as a second inlet channel, passes through the first manifold 504, and is discharged through connection channel 511 acting as a second outlet channel. Symmetrically thereto, reagent is simultaneously injected from connection channel 514 acting as a second inlet channel, passes through the second manifold 505, and is discharged through connection channel 515 acting as a second outlet channel. The flow and pressure in both manifolds 504, 505 may be controlled independently, and is adjusted to bypass the reagent channels 502 such that the macromolecule containers are fluidically immobilised in the stagnant volume of the reaction channels 502. Typically in practice, this is done by balancing the pressure in the two manifolds 504, 505 so as to achieve substantially equal pressures on either end of each of the reaction channels 502.

Figure 10:
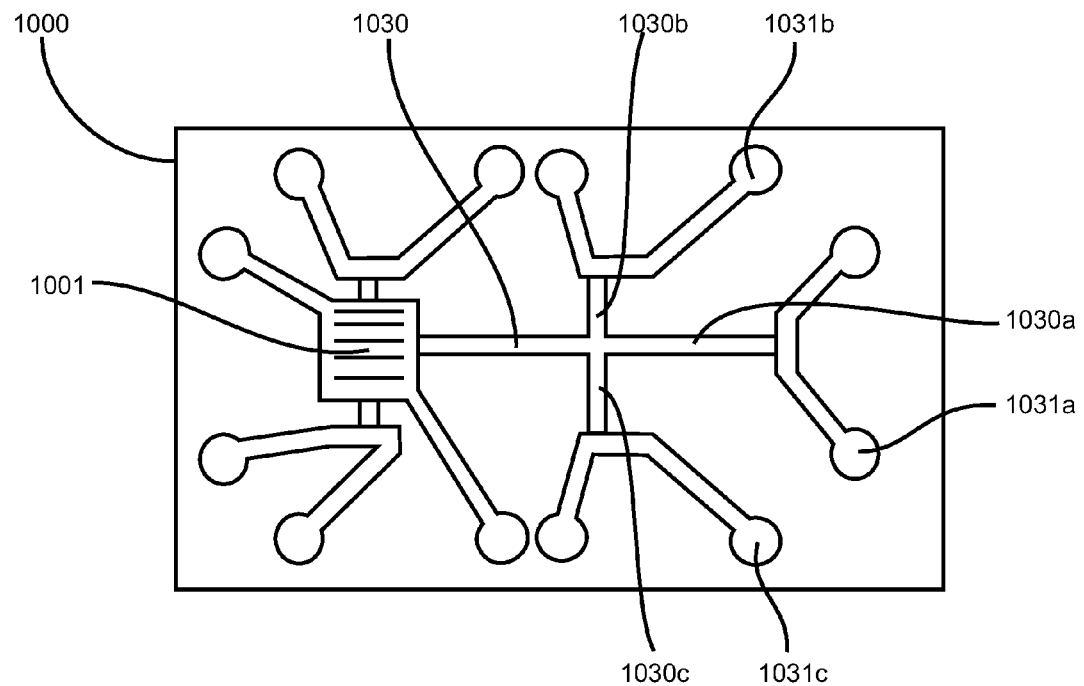

Referring to FIG. 10, a microfluidic device 1000 according to a further embodiment may comprise a first component for trapping/isolating macromolecule containers and releasing a single macromolecule therefrom by means of an enzymatic reaction in a reaction chamber 1001. Advantageously, the first component may essentially correspond to the above-mentioned embodiments, e.g. as described with reference to FIG. 1-4. The released macromolecule may be shunted to an extraction channel 1030, and passed to a subsequent second component of the device 1000, arranged in direct extension of the extraction channel 1030. The second component comprises a first nanoslit 1030a, a second nanoslit, 1030b, and a third nanoslit 1030c, which together with the nanoslit of the extraction channel 1030 form a cross with a longitudinal axis defined by two channels 1030 and 1030a, and a transverse axis perpendicular thereto by the two other channels 1030b, 1030c. The channels 1030a-c may be accessed through fluidic interface ports 1031a-c. The nanoslits 1030, and 1030a-c have typically the same height of up to a few hundred nanometers, typically about 100 nm, depending on the actual application. The width of the channels may be between a few micrometers up to a couple of hundred micrometers, typically about 50 µm, compatible with state-of-the-art microscale pattern transfer techniques.

The longitudinal channels 1030, 1030a of the cross in the second component may be used to linearize, stretch, observe/sequence, label or otherwise analyse/process the single macromolecule produced in the first component. The transverse channels 1030b, 1030c may be used for fluidic manipulation of the macromolecule, and/or for providing additional reagents as required by the processes performed in the second component. The combination of the first and the second component in the integrated device 1000 of FIG. 10 has the advantage that the analysis/processing steps in the second component benefit from the ultra-long macromolecules that are produced in the first component.

EXAMPLE

Figure 7:
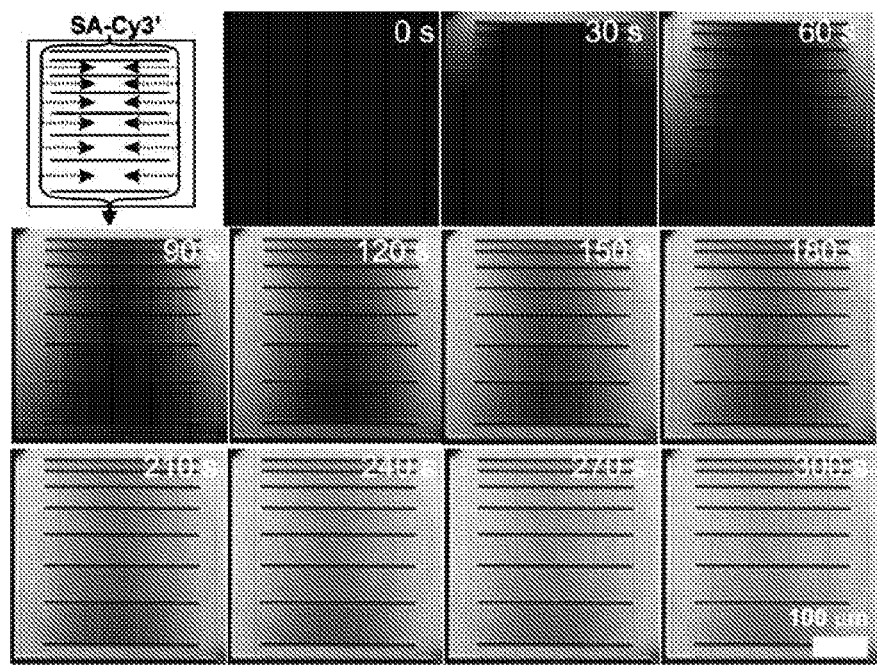
Figure 8:
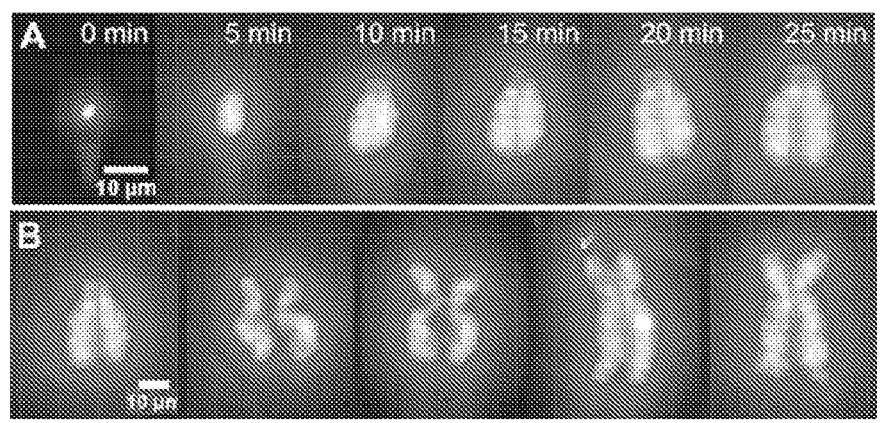
Figure 9:
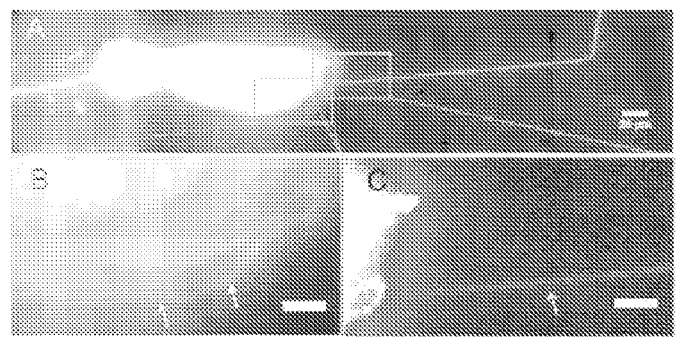

Referring to FIGS. 6a-6d, 7, 8 and 9, in the following, an example is given for the design, fabrication and use of a device for handling and releasing DNA from metaphase chromosomes. FIG. 6 gives a schematic view of the device used in the example and its operation. FIGS. 7-9 show micrographs visualising different aspects of the operation of the device. The device design of the example aims to immobilize a single metaphase chromosome in an isolation zone through which reagents can be exchanged by diffusion enabling proteins to be digested. The DNA thus extracted can then be shunted out of the isolation zone into a nanoslit for stretching.

FIG. 6 shows schematically a sequence of operational states for a device according to another embodiment of the invention. The device of FIG. 6 has, apart from the number of reaction channels 602, the same configuration of the reaction chamber region, and in particular of the first inlet/outlet channels 610, 611, the second inlet/outlet channels 620, 621, and the extraction channel 630. The sequence shows in FIG. 6a loading of a sample 650 containing metaphase chromosomes 651. The sample 650 is loaded at an input port 612, which is connected to the reaction chamber 601 via first inlet channel 610. Referring to FIG. 6b, the reaction chamber 601 is filled with the sample 650 by establishing a diagonal sample flow through the reaction chamber 601: a sample injection flow 660 through first inlet channel 610 transfers the sample fluid 650 to a first manifold flow 661. The first manifold flow 661 branches into a number of reaction channel flows 662. After passing the reaction channels 602, the reaction channel flows 662 are collected by a second manifold flow 663, which is leaves the reaction chamber in a sample discharge flow 664. Single chromosomes 651 carried by the reaction channel flows 662 may be observed by optical microscopy, and the sample flow may be stopped when the presence of an isolated target chromosome 651 is determined. FIG. 6c shows how protease is introduced in the reaction chamber 601 without displacing the chromosome 651 of interest by establishing a pressure balanced parallel flow through the manifolds 604, 605. A reagent injection flow 670 carrying protease splits essentially symmetrically into a first manifold flow 671 and a second manifold flow 672, and recombines again before leaving the reaction chamber 601 in a reagent discharge flow 674. The manifolds flows 671, 672 essentially by-pass the reaction channels 602. The protease enters the reaction channels 602 by diffusion 672 to act on the immobilised target chromosome 651 in order to release a DNA molecule 652. In FIG. 6d, the released DNA 652 is retrieved from the reaction channel 602 and shunted to the extraction port 630 by applying appropriate shunting pressures 680, 681, 682, 683 through the connection channels 610, 611, 620, and 621, respectively. The released DNA 652 is stretched through a 100 nm high, 450 µm long and 50 µm wide nanoslit forming the extraction channel 630.

The device was designed, with the aid of finite element simulations (COMSOL, USA), to have a series of isolation zones to slow down the chromosomes in the trap area while maintaining a high flow rate through the device. The parallel isolation zones increased in area with increasing distance (3000 µm$^2$, 6000 µm$^2$, 9000 µm$^2$, etc.) from the sample entry point, in order to obtain a homogeneous flow rate into each of the zones during the introduction of the sample. This was to ensure that all chromosomes entering isolation zones were moving at the same horizontal speed in order to facilitate selection of individual chromosomes from the parade of chromosomes and cell debris flowing through the device.

The device was fabricated using UV lithography and reactive ion etching of a silicon substrate. Briefly, a 500 nm dry thermal oxide was grown on a silicon wafer. The protease inlet slit and the slit for DNA stretching were defined by UV masking and deep reactive ion etching in the oxide at the depth of 500 nm and 100 nm, respectively. The 50 µm wide microfluidic channels connecting the inlet ports and the 400× 400 µm trap area were defined using a third UV lithography step and were etched in silicon at a depth of 10 µm. A thermal oxide was grown in order to later allow fusion bonding. Inlet holes were made by powder blasting from the backside of the device which was finally sealed by fusion bonding to a 500 µm thick borofloat glass wafer.

FIG. 7 visualizes the filling of the manifolds with an enzymatic reagent and the diffusion thereof into the reaction channels. The protease reagent was introduced from the second inlet port (located at the top edge of the frames) with flow occurring perpendicular to the reaction channels acting as isolation zones for the isolation of individual chromosomes. In this configuration there was no flow into the isolation zones; reagent exchange with the stagnant volume inside the isolation zones occurred by diffusion only. We used streptavidin labelled with Cy3 to visualize the diffusion of the reagent into the isolation zones to verify device operation before chromosome isolation and protease digestion was conducted. Observation of the introduction and spread of the Cy3 fluorescent marker into the isolation zones validated the device design and indicated that the reagent is able to spread quite well throughout the isolation zones by time, 300 s. The sequence of micrographs was taken with a time-lapse of 30 s between frames and shows the increasing fluorescence in the reaction chamber ("trap area") due to the diffusion of stretavidin-Cy3 as it is injected at 0.6 nL min$^{-1}$. The diffusion constant is $60 \times 10^{-12}$ m$^2$ s$^{-1}$.

After experimental verification of the device design, the sample and reagent exchange process was applied to a sample containing metaphase chromosomes. The chromosomes were isolated from Jurkat cells (DSMZ, Germany: ACC282) in a polyamine buffer as described by Cram et al. (L. S. Cram, C. S. Bell and J. J. Fawcett, Methods Cell Sci., 2002, 24, 27-35) with some modifications. Briefly, the Jurkat cells were grown at 37° C. in a 5% CO$_2$ atmosphere. At exponential growth, they were arrested in metaphase with colcemide at 0.06 μg mL$^{-1}$ for 12-16 hours. The cells were collected at 200 g for 10 minutes and re-suspended in a swelling buffer (55 mM NaNO$_3$, 55 mM CH$_3$COONa, 55 mM KCl, 0.5 mM spermidine, 0.2 mM spermine) at approximately 10$^6$ cells per mL and incubated for 45 minutes at 37° C. The swollen cells were collected at 200 g for 10 minutes and re-suspended in an ice-cold isolation buffer (15 mM Tris-HCl, 2 mM EDTA, 80 mM KCl, 20 mM NaCl, 0.5 mM EGTA, 0.5 mM spermidine, 0.2 mM spermine, 0.12% digitonin, and 7 mM mercaptoethanol) at approximately 8×10$^6$ cells per mL. The cells were lysed by vigorous vortex for 30 s. The chromosome content was estimated to be in the order of 10$^7$ cells per mL.

The device was mounted on a holder interfacing the inlet holes of the device with pressured air allowing movement of the solution inside the device as described elsewhere (W. Reisner, N. B. Larsen, H. Flyvbjerg, J. O. Tegenfeldt and A. Kristensen, Proc. Natl. Acad. Sci. U.S.A., 2009, 106, 79-84). Fluorescence imaging was performed using an inverted microscope (Nikon Eclipse TE2000, Japan) equipped with a 60×/1.00 water immersion objective and an EMCCD camera (Photometrics Cascade II512, USA). The temperature inside the device was controlled by a cartridge heater held in contact with the backside of the silicon device. Inlet holes were loaded with 30 mL of solution unless otherwise mentioned.

Prior to receiving the chromosomes 651, the device was flushed by 1% sodium dodecyl sulfate, buffer solution (0.5_ TBE, 3% b-mercaptoethanol (BME) and 0.5% Triton X-100) and BSA at 1 mg mL$^{-1}$ for 10 minutes. A sample 650 with 1000-2000 chromosomes 651 were added to the diagonal sample inlet port 612; the depth of the microfluidic structure allowed the cell extract to be flushed quickly through the isolation zones formed by the reaction channels 602 while watching for the appearance of chromosomes 651 that could be isolated. A single chromosome 651 was trapped in a reaction channel 602 of the device.

Simultaneously the temperature was adjusted to 37° C. and a 100 μg mL$^{-1}$ solution of protease K (1 mM of YOYO-1 is added to the protease K solution for staining the DNA strands while cut free from the chromatin in the vicinity of the bright chromosome body) was introduced. The device enabled a high flow rate of 0.6 nL min$^{-1}$ allowing the protease to diffuse quickly into the stagnant volume within the isolation zone 602.

Moreover, a continuous flow 670, 671, 672, 673, 674 through the device ensured that after 4 minutes the protease concentration around the isolated chromosome 651 was maintained above 50 μg mL$^{-1}$ and that the digestion products were washed away from the isolation zone through diffusion.

The series of micrographs in FIG. 8 (A) shows the digestion of a single metaphase chromosome 651 with protease at 37° C. Subsequent frames are taken with a time-lapse of 5 minutes. As proteolysis took place, the chromosome 651 swelled and self-aligned in the plane of the device allowing reliable and reproducible fluorescence time-lapse imaging. Although no visible change of the chromosome 651 was observed after t=25 minutes, digestion was allowed to proceed for one hour as recommended by protocols for digestion in bulk solution (J. Sambrook, E. F. Fritsch and T. Maniatis, Molecular Cloning: a Laboratory Manual, Cold Spring Harbor Laboratory, 1989). FIG. 8 (B) shows different individually isolated chromosomes after 40 minutes digestion. Even after a digestion treatment that should be sufficient to remove all proteins, sister chromatids could still be clearly identified and chromosomes of different sizes and with different centromere positions could be seen. Moreover heterogeneity in the chromatin folding morphology could be observed at the micrometer scale.

The chromosomal DNA 652 could be easily manipulated by using the sample inlet/outlet microchannels 610, 611 and the reagent inlet/outlet slits 620, 621 as a bi-directional flow system inside the reaction chamber 601. This enabled the chromosomal DNA 652 to be moved in front of the 100 nm high nanoslit forming the extraction channel 630 and then forced in. Although, the bi-directional flow in the reaction chamber 601 would enable DNA 652 extracted from chromosomes 651 trapped in different isolation zones 602 to each be individually manipulated and moved toward the extraction channel 630, in the present example a dilute solution of chromosomes 651 was used and only one chromosome 651 at a time was processed.

After completion of the digestion, DNA 652 released from an individual chromosome 651 is passed through a 100 nm high nanoslit forming the extraction channel 630. FIG. 9A shows a micrograph of a released DNA molecule 652 being shunted to the extraction channel 630; The post-digestion chromosomal DNA 652 was observed as a densely packed core composed of separated loops. The chromosomal DNA 652 was highly pliable: the DNA 652 stretched by increasing the flow through the nanoslit 630 and recoiled when the flow was stopped.

FIG. 9B and FIG. 9C show micrographs with details of the released DNA molecule 652 in the extraction channel 630. FIG. 9B is a close-up of loops of DNA emanating from the core package of the chromosomal DNA. FIG. 9C is a close-up of the linear DNA strand emerging from the DNA package. A longer separate strand stretched across the whole length of the 450 μm long nanoslit and out into a microchannel (FIG. 4C). This corresponded to a minimal length of about 1.3 Mbp (1.3 million bases) of fully elongated DNA. Such separated DNA strands were also visible around the chromosomal DNA before the introduction to the nanoslit.

LIST OF REFERENCE NUMBERS

Throughout the application, like numerals refer to like parts, wherein x is to be replaced by the numbers 1, 2, 3 . . . 10 as appropriate.

x00 device
x01 reaction chamber
x02 reaction channel
x03 flow barrier
x04, x05 first and second manifold
x06-x09 first, second, third and fourth edges
x10, x11 inlet/outlet channel
x12, x13 connection ports
x14, x15 inlet outlet channel
x20, x21 inlet/outlet channel
x22, x23 connection ports
x30 extraction channel
x31 connection port
x40, x41 device parts
x42, x43 connection holes
x50 sample
x51 macromolecule container
x52 macromolecule
x60-x64 sample flow
x70, x71 reagent flow
x72 reagent diffusion
x73, x74 reagent flow
x80-x83 fluidic manipulation
x98, x99 edge channels 1030a-c nanoslits
1031a-c connection ports
M symmetry axis

The invention claimed is:

1. A microfluidic device for enzymatic processing of macromolecules, the device comprising
    a reaction chamber comprising a first manifold, a second manifold, and a plurality of reaction channels defined by predominantly continuous flow barriers, each reaction channel extending from the first manifold to the second manifold, wherein reaction channel walls are defined by the flow barriers,
    a first inlet channel and a first outlet channel for filling the reaction channels via the manifolds with one or more macromolecule containers suspended in a first carrier fluid, wherein the one or more macromolecule containers is a cell, a cell nucleus or metaphase chromosome encapsulating the macromolecules therein, wherein the first inlet channel and the first outlet channel are configured such that a flow established from the first inlet channel to the first outlet channel is guided through the reaction channels, wherein the reaction channels increase in width from the first inlet channel to the first outlet channel for decreasing the flow resistance from the first inlet channel towards the first outlet channel, and
    a second inlet channel and a second outlet channels for feeding an enzymatic reagent to the reaction chamber essentially without displacing the macromolecule containers trapped in the reaction channels, wherein addition of the enzymatic reagent releases substantially intact macromolecules from the macromolecule containers, wherein the second inlet channel and the second outlet channel are configured such that a flow established from the second inlet channel to the second outlet channel is guided through at least one of the manifolds and bypasses the reaction channels.

2. The microfluidic device according to claim 1, wherein the reaction chamber is essentially symmetric with respect to a mirror axis connecting said second inlet channel and said second outlet channel, a longitudinal axis of the reaction channels being oriented essentially transverse to the mirror axis.

3. The microfluidic device according to claim 1, wherein the device is provided with a viewport in the region of the reaction channels, the view port allowing for the visual, electrical and/or magnetic detection of one or more macromolecule containers in at least one of the reaction channels.

4. The microfluidic device according to claim 1, wherein a total effective cross-sectional area for flow through the reaction chamber in the region of the reaction channels is enlarged as compared to the first inlet channel by a ratio of at least 2:1, alternatively at least 5:1, or alternatively at least 10:1.

5. The microfluidic device according to claim 1, wherein a flow resistance of reaction channels is decreased with increasing distance from the first inlet channel.

6. The microfluidic device according to claim 1, wherein the device only comprises passive microfluidic components.

7. The microfluidic device according to claim 1, wherein the reaction chamber has a rectangular layout, the rectangle having a first edge, a second edge parallel thereto, and a third and a fourth edge essentially perpendicular to the first and second edges,
    the first and second manifold extending along the first and second edge, respectively,
    the reaction channels extending from the first to the second manifold in a direction essentially parallel to the third and fourth edge,
    the first inlet channel and the first outlet channel being arranged at diagonally opposing corners of the rectangle, and
    the second inlet channel and the second outlet channel being arranged at the third and fourth edges respectively, wherein both the second inlet channel and the second outlet channel are in symmetric fluid communication with both the first and the second manifolds through edge channels extending parallel to the reaction channels along the third and fourth edges.

8. The microfluidic device according to claim 1, wherein the device further comprises an extraction channel connected to one of the manifolds.

9. The microfluidic device according to claim 1, wherein the first inlet channel is aligned such that an angle of injection of fluid from the first inlet channel into the reaction chamber is between 10 to 90 degrees, preferably 30 to 60 degrees, relative to the flow barriers.

10. The microfluidic device according to claim 1, further comprising an extraction channel connected to one of the manifolds, wherein the extraction channel has a width larger than 4 µm and a depth between 50 nm and 100 nm.

11. A method for preparing isolated macromolecules, using the microfluidic device according to claim 1, the method comprising the steps of
    a) at an input port connected to the first inlet channel, providing a first fluid containing macromolecule containers, wherein the macromolecule container is a cell, a cell nucleus or metaphase chromosome,
    b) establishing a flow of the first fluid from the first inlet channel, via the first manifold, through the reaction channels, and via the second manifold to the first outlet channel,
    c) stopping the flow when at least one of the macromolecule containers is detected in at least one of the reaction channels, thereby trapping the at least one macromolecule container in the at least one reaction channel,
    d) at an input port connected to the second inlet channel, providing a second fluid containing an enzymatic reagent,
    e) in at least one of the manifolds, replacing the first fluid by the second fluid by establishing a flow from the second inlet channel to the second outlet channel, wherein the flow of the second fluid essentially by-passes the reaction channels, and
    f) allowing the enzymatic reagent to diffuse from the at least one manifold into the reaction channels to perform an enzymatic reaction releasing at least one substantially intact isolated macromolecule from the at least one macromolecule container.

12. The method according to claim 11, wherein the macromolecule container is a metaphase chromosome and the macromolecule is a DNA-molecule.

13. The method according to claim 11, wherein a pre-defined level of enzyme concentration is maintained in the at least one manifold by maintaining in the at least one manifold a continuous flow of reagent with a pre-defined enzyme concentration.

14. The method according to claim 11, wherein in step c), trapping of the macromolecule container in one of the reaction channels is visually detected by an operator and/or by means of a machine capable of automated target detection based on visual, electrical, and/or magnetic sensors.

15. The method according to claim 11, wherein in step e) the first fluid is replaced by the second fluid essentially simultaneously in both manifolds, wherein at least for the reaction channel comprising the trapped macromolecule container, the hydrostatic pressures on either end of said reaction channel are balanced during said replacement.

16. The method according to claim 11, further comprising the step of
g) transferring the isolated macromolecule via an extraction port to a subsequent processing step, such as sequencing and/or amplification.

* * * * *